(12) United States Patent
Rassoli

(10) Patent No.: US 6,923,648 B1
(45) Date of Patent: Aug. 2, 2005

(54) DENTAL IMPLANT FASTENER SYSTEM

(76) Inventor: Jeff Rassoli, 2737 E. Regal Park Ave., Anaheim, CA (US) 92806

( * ) Notice: Subject to any disclaimer, the term of this patent is extended or adjusted under 35 U.S.C. 154(b) by 0 days.

(21) Appl. No.: 10/421,596

(22) Filed: Apr. 22, 2003

(51) Int. Cl.$^7$ ............................................... A61C 3/00
(52) U.S. Cl. ..................................................... 433/173
(58) Field of Search ............................... 433/172, 173, 433/174, 175, 176; 81/459

(56) References Cited

U.S. PATENT DOCUMENTS

| | | | | |
|---|---|---|---|---|
| 680,560 | A * | 8/1901 | Barnes | 81/459 |
| 4,579,531 | A * | 4/1986 | Hinks | 433/225 |
| 4,995,810 | A * | 2/1991 | Soderberg | 433/141 |
| 5,513,545 | A * | 5/1996 | George | 81/53.2 |
| 5,571,015 | A * | 11/1996 | Siegmund | 433/173 |
| 5,591,029 | A * | 1/1997 | Zuest | 433/173 |

OTHER PUBLICATIONS

Sulzer Medica, Sulzer Dental Inc., Price List & Ordering Information; 2001, cover and p. 9.
DiamoDent Restorative Catalog, Fourth Edition May 2002 Cover and pp 2, 3&4, 7&8, 9&10.
Advent and Screw-Vent Implant Systems, Technical Information and Product Catalog, Paragon, Implant Co., Mar., 2000, Cover and pp. 2, 4, 5, 15.
Taper-Lock External Hex System, Product Selection Guide and Catalog, Paragon Implant Co., Feb. 1998, Cover and pp 13, 15.

* cited by examiner

*Primary Examiner*—Cary E. O'Connor
(74) *Attorney, Agent, or Firm*—Charles H. Thomas

(57) ABSTRACT

An endosseous dental implant fastening system is provided with a fastening screw that is configured to prevent complete disengagement of the fastening screw from a screw extraction tool during removal of the screw from threaded engagement with the implant and abutment members. A fastening screw is modified from conventional construction by providing the mouth of the socket in the head of the screw that is utilized to rotate the screw with left-hand threads, and to provide an installation and removal tool with a shank having corresponding left-hand threads at it distal tip. Counterclockwise rotation of the installation and removal tool relative to the fastening screw causes the distal tip of the installation and removal tool to advance into engagement with the left-hand threads defined in the socket of the fastening screw. The fastening screw is thereby temporarily attached to the installation and removal tool during installation and removal of the fastening screw.

14 Claims, 8 Drawing Sheets

DENTAL IMPLANT FASTENER SYSTEM

BACKGROUND OF THE INVENTION

1. Field of the Invention

The present invention relates to osseodontic dental implant systems for tooth replacement in orthodontic patients.

2. Description of the Prior Art

In the field of orthodontics there are several techniques for tooth replacement. Crowns are widely employed for this purpose. However, dental crowns require a sturdy foundation. In the simplest, most desirable and least costly procedure the natural structure of the root of a tooth is utilized as the foundation to which the crown is anchored. However, in some instances, this is impractical since a tooth may be so badly damaged due to disease or injury that the entire tooth must be removed.

In such a situation one option is the use of an endosseous dental implant system. In such a system an implant member is inserted into the jaw of a patient. Very typically the implant member will be externally threaded with self-tapping screw threads that anchor the implant member into the bone of the jaw underlying the patient's gums. The implant member may be internally tapped to receive a fastening screw.

The implant member has opposing gingival and osseous ends. That is, the implant member is of a generally cylindrical, externally threaded configuration with an internally tapped blind bore therein. The open end of the bore is at the gingival end of the implant member which resides at the patient's gum when the implant member is installed. The opposite, osseous end penetrates into the bone structure of the patient's jaw.

A conventional osseous dental implant system also includes an abutment member. The abutment member also has opposing ends which may be referred to as the gingival and coping support ends. The gingival end of the abutment member faces and mates with the gingival end of the implant member. The abutment member includes an internal, longitudinal bore with openings at both of its ends and with a bearing ledge defined within its structure. A coping, which is an artificial tooth or crown, is ultimately permanently attached to the coping support end of the abutment. A screw is utilized to attach the abutment member to the implant member. The externally threaded shank of the screw extends through the longitudinal passageway defined through the structure of the abutment member and is threadably engaged with the internal threads of the blind, tapped bore in the implant member. The head of the screw rests upon the bearing ledge in the structure of the abutment member to firmly, and ultimately permanently, attach the abutment member to the implant member.

A conventional endosseous dental implant fastening screw is formed with a head having a cylindrical outer surface configuration and a shank of smaller diameter externally threaded with male, right-hand threads throughout its length. At the center of the top of the head a socket or cavity of noncircular cross section is formed to receive the distal end of a fastening tool. Very typically the socket has a hexagonal cross-sectional shape, as does the distal tip of the fastening tool. The slender shank of the fastening tool fits within the narrow passageway formed through the abutment and the hexagonal tip at the distal end of the fastening tool engages the walls of the socket in the screw head so as to allow the screw to be rotated by turning the grip of the fastening tool. The shank of the fasting tool is slender enough to fit into the narrow, open end of the passageway formed through the abutment.

With the distal tip of the fastening tool engaged in the socket of the screw, the screw is inserted into the abutment passageway and guided longitudinally along until the externally threaded shank of the dental implant fastening screw reaches an internally threaded, necked-down region of the abutment passageway. This necked-down region forms an outwardly facing, annular bearing ledge that forms a seat for the underside of the head of the dental implant fastening screw adjacent its shank.

By rotating the fastening tool in a clockwise direction, the right-hand, spiral threads of the fastening screw are advanced into engagement with the internal, female threads at the necked-down region of the abutment passageway. Advancement of the fastening screw is continued by rotating it in a clockwise direction until the distal extremity of the dental implant fastening screw reaches the internal threads of the dental implant member. Continued clockwise rotation of the fastening tool advances the threads on the shank of the dental implant fastening screw into engagement with the internal threads of the dental implant. Tightening is continued in this manner until the annular face of the head of the dental implant fastening screw adjacent the shank thereof arrives in abutting relationship against the annular screw seat defined within the abutment in the longitudinal passageway that extends through the entire length of the abutment. Because the distal tip of the fastener installation tool has a noncircular cross section that fits snugly into a socket in the screw head of a corresponding shape, continued rotation of the grip securely tightens the threads of the dental implant fastening screw into the mating, female threads of the dental implant. Once the fastening screw has been tightened, the tip of the fastener installation tool may be pulled longitudinally out of the hexagonal socket defined in the exposed end of the head of the dental implant fastening screw.

While a conventional dental implant screw fastener installation tool operates quite well to tighten dental implant fastening screws in position, it is sometime necessary to remove the dental implant fastening screw for various reasons. In conventional practice the same fastener installation tool is employed. That is, the distal, hexagonal tip of the fastener installation tool is inserted into the corresponding hexagonal-shaped socket formed in the head of the fastening screw and the grip of the fastener installation tool is counterrotated, in a counterclockwise direction. The shank of the dental implant fastening screw is thereupon threadably disengaged from the female threads of the dental implant member, and subsequently from the female threads of the abutment.

The progressive withdrawal of the fastening screw proceeds without difficulty as long as there is engagement between the threads of the fastener screw and those of either the implant or the abutment. However, at some point the threads on the shank of the fastening screw disengage completely from the internal threads in the necked-down region of the abutment. This disengagement typically occurs well before the head of the fastening screw is accessible from outside the passageway opening of the abutment.

Without thread engagement during counterclockwise rotation of the fastening screw relative to the abutment, there is no force urging the fastening screw out toward the open end of the abutment passageway, even if the rotation of the fastener installation tool in a counterclockwise direction is continued. To the contrary, while the fastening screw can be rotated, it rotates freely within the confines of the smoothwalled cylindrical portion of the passageway and cannot easily be withdrawn further. If one attempts to merely withdraw the shank of the fastening tool out of the open end of the passageway in the abutment, the hexagonal tip at the distal end of the fastening tool is merely pulled longitudinally out of the hexagonal socket, leaving the fastening screw within the confines of the longitudinal passageway through the abutment.

In a typical conventional practice, it is necessary to create some type of frictional engagement between the distal tip of the fastener installation tool and the socket in the head of the fastening screw in a longitudinal direction. This is sometimes achieved by inserting a toothpick longitudinally into the open end of the passageway alongside the shank of the fastening tool to attempt to grip some location on the peripheral end of the head of the fastening screw between the toothpick and the shank of the fastener installation tool. That is, the shank of the fastener installation tool and the toothpick are utilized somewhat in the manner of tongs to attempt to grip a peripheral location on the head of the fastening screw to allow complete withdrawal of the fastening screw from the abutment passageway. This procedure is somewhat awkward and requires considerable practice to master the technique.

Another approach that has been taken is to put a small amount of wax on the end of the distal tip of the fastener installation tool before the shank of the fastener installation tool is inserted into the socket formed in the dental implant fastening screw head. The wax acts as sort of a temporary adhesive between the distal tip of the fastening tool and the socket in the dental implant screw head. However, this technique also requires considerable patience, since the adhesive bond of the wax to the fastening tool and to the socket of the screw head is necessarily quite weak.

SUMMARY OF THE INVENTION

The present invention solves the problem of difficulty in completely withdrawing a fastening screw from the longitudinal passageway of a dental implant abutment by modifying the configuration of the fastening screw. More specifically, while the head of the fastening screw is still provided with a socket of noncircular cross section, such as a hexagonal cross section, in the deepest depths of the socket formed in the head, internal threads in an opposite spiral direction are formed into the walls of the socket at its open mouth. That is, a few internal, left-hand female threads are formed adjacent the opening at the mouth of the socket.

In addition, a novel dental implant installation and extraction tool is provided that is utilized in conjunction with the conventional dental implant fastener installation tool. The installation and extraction tool of the present invention has a narrow, elongated shank with a distal tip upon which external, left-hand male threads are formed. At an intermediate location on the shank external, male, right-hand threads are formed having the same pitch and diameter as the internal right-hand female threads formed at the necked-down region of the abutment passageway, and also the internal, right-hand female dental implant threads formed in the implant itself.

The term "right-hand" as applied to the engageable threads described herein means that the threads are configured so that advancement of the fastener screw or installation and removal tool toward the implant member is achieved by rotation of the fastener screw or tool in a clockwise direction. Conversely, rotation of the installation and retraction tool in a counterclockwise direction advances the tool toward the socket in the screw head (and toward the implant member) to engage "left-hand" threads at the mouth of the screw head socket.

To extract a dental implant fastening screw which tightly engages an abutment to a dental implant member, a conventional fastener installation tool having a distal tip of noncircular cross section is first employed to loosen the tight interconnection of the shank of the fastening screw with the dental implant member. That is, the hexagonal tip of the conventional implant fastener installation tool is inserted past the internally threaded mouth of the fastening screw socket and into engagement with the hexagonal portion of the socket lying beyond the mouth. The conventional fastener installation tool is thereupon rotated in a counterclockwise direction, thus partially loosening the implant fastening screw.

However, at this point the conventional tool is removed and the novel dental implant screw installation and extraction tool of the invention is inserted into the abutment passageway in place thereof and advanced longitudinally until the distal tip of the extraction tool reaches the open mouth of the socket in the head of the fastening screw. The left-hand, male threads on the distal tip of the extraction tool can then be engaged with the left-hand female threads formed in the mouth of the socket by rotating the extraction tool in a counterclockwise direction. When the left-hand threads on the distal tip of the extraction tool and in the mouth of the socket of the dental implant screw head mate with each other, this rotation screws the distal tip of the extraction tool into the open mouth of the fastening screw head.

This counterclockwise rotation of the tool of the invention also acts upon the right-hand threads of the shank of the fastening screw to disengage the fastening screw first from the internal threads within the dental implant member, and then from the internal threads in the necked-down portion of the abutment passageway. While effectuating disengagement of the right-hand threads of the dental implant fastening screw from the dental implant and from the abutment, the engaged left-hand screw threads of the extraction tool and those at the mouth of the socket in the fastening screw head ensure that the fastening screw head remains securely joined to the installation and extraction tool. The fastening screw can thereby easily be withdrawn longitudinally from within the confines of the elongated passageway defined within the abutment. The difficulty of dislodgment of the fastening screw from the end of the tool used to manipulate it once the screw threads on the shank of the fastening screw have been disengaged from both the threads of the dental implant and the threads of the abutment is thereby outcome.

A primary object of the present invention is to provide an endosseous dental implant system with a coupling that allows the fastening screw to be joined to the tip of a tool utilized to maneuver the fastening screw into position for engagement with the dental implant and to extract it from within the confines of the abutment when the fastening screw is to be removed.

A related object of the invention is to provide a releaseable coupling between a fastening screw and a manipulating tool that holds the shank of the fastening screw in longitudinal alignment with the shank of the manipulating tool during insertion and removal of the dental implant fastening screw relative to a dental implant and its associated abutment.

In one broad aspect the present invention may be considered to be an improved endosseous dental implant fastening screw. As with conventional dental implant fastening screws, the improved fastening screw of the invention has a shank with right-hand male threads defined thereon and a fastening screw head located atop the shank and formed with an axial socket therein. The socket has a noncylindrical cavity located internally within the fastening screw head in longitudinal alignment with the fastening screw shank. This noncylindrical cavity may, for example, have a hexagonal, square, or star-shaped cross-sectional configuration like conventional sockets formed in conventional dental implant fastening screw heads. Unlike conventional dental implant fastening screws, however, the socket in the head of the fastening screw of the invention has a mouth at which internal female left-hand threads are formed.

By providing threads at the mouth of the socket that are oriented in a spiral direction opposite to those threads on the shank of the fastening screw a system is provided that allows the head of the fastening screw to be held releaseably secured to the tip of a manipulating tool while disengaging the fastening screw from the endosseous implant.

Clockwise rotation and advancement of the installation and removal tool causes the right-hand threads on the shank of the fastening screw to engage the corresponding right-hand threads in the implant and abutment members. Once a preliminary level of tightness has been achieved, continued clockwise rotation of the installation and removal tool of the invention disengages that tool from the head of the dental implant fastening screw and the screw is fully tightened utilizing a conventional installation tool.

The fastening screw can easily be removed utilizing the installation and removal tool of the invention by advancing the installation and removal tool into the fastener, and rotating it in a counterclockwise direction to engage the left-hand threads to join the fastener head to the distal tip of the installation and removal tool. Continued counterclockwise rotation backs the fastening screw out of engagement with the implant and abutment members while holding the fastening screw firmly in position on the distal tip of the installation and removal tool.

In another broad aspect the invention may be considered to be an improved endosseous dental implant system comprising: an endosseous dental implant member; a mating abutment member; and a fastening screw having a head with a shank depending therefrom. The endosseous dental implant member of the invention has a longitudinal bore with internal right-hand female implant screw threads defined therein. The mating abutment member has a longitudinal passageway defined throughout its length. The implant passageway is longitudinally aligned with the bore in the dental implant member. The implant passageway has an upper end of enlarged diameter thereby defining an upwardly facing annular screw head bearing ledge. The fastening screw shank has right-hand threads thereon engageable with both the implant screw heads and the abutment screw threads. The fastening screw head has an upwardly facing, noncylindrical socket formed with a mouth to the socket having internal left-hand threads defined thereon.

The invention may further be considered to be comprised of an installation and extraction tool for engaging the mouth of the socket. This installation and extraction tool is comprised of a grip with a shank extending therefrom formed as a screw extraction rod having a distal tip. External, male, left-hand threads engageable with the left-hand threads at the socket mouth of the fastening screw are formed on the distal tip of the shank of the installation and extraction tool. The noncylindrical socket in the screw head preferably has a hexagonal cross section. The extraction rod may have external, male, right-hand threads threadeably engageable with the implant screw threads formed on the extraction rod in longitudinal displacement from the distal tip.

In still another aspect the invention may be considered to be an endosseous dental implant apparatus comprising: an endosseous dental implant member; a mating abutment member; and an implant fastening screw. The endosseous dental implant member has a longitudinal bore with internal right-hand female implant threads defined thereon. The mating abutment member has a longitudinal passageway defined throughout its length. The implant bore and the abutment passageway are longitudinally aligned with each other. The abutment passageway has a mouth of enlarged cross section remote from the implant and an annular fastening screw head bearing ledge is defined at the mouth of the passageway.

The implant fastening screw has a head and a shank depending therefrom. The shank has external right-hand male fastener threads defined thereon. The head has a longitudinally extending socket defined therein, including a mouth portion with female left-hand threads defined therein and a portion of noncircular cross-sectional area beneath the mouth. This noncircular portion preferably has a hexagonal shape.

The invention may also be considered to be an endosseous dental implant fastening screw insertion and removal tool having a grip and an elongated rod with a distal tip remote from the grip. Left-hand male threads are formed on the distal tip of the elongated rod for engaging the left-hand female threads at the mouth portion of the socket. Male right-hand threads formed externally on the elongated rod between the lift-hand threads and the grip threads.

The invention may be described with greater clarity and particularity by reference to the accompanying drawings.

DESCRIPTION OF THE EMBODIMENT

Figure 1:
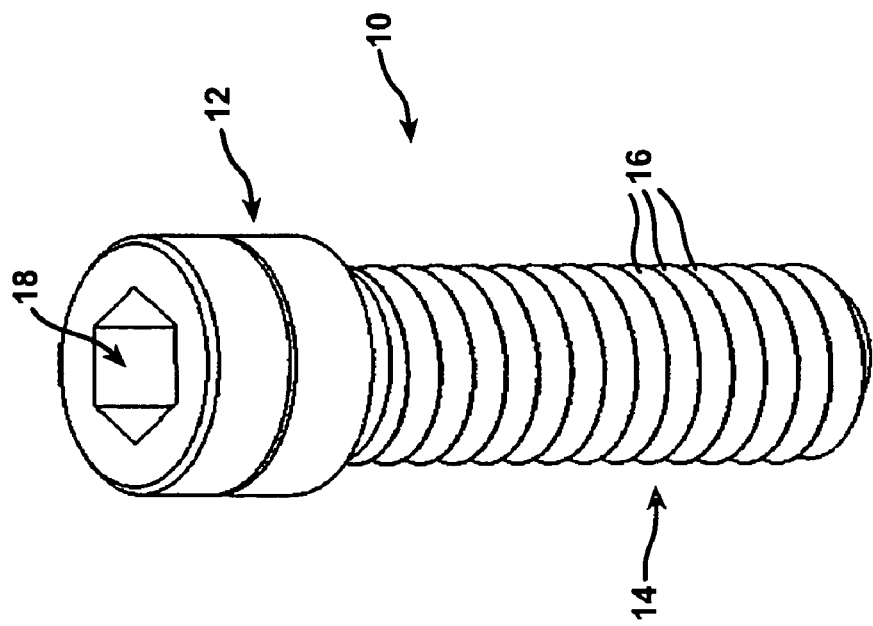
FIG. 1 is a perspective view of a conventional dental implant fastening screw.

FIG. 1 is a perspective view illustrating a conventional osseodontic dental implant fastening screw 10. The fastening screw 10 is provided with a head 12 having a generally cylindrical outer surface configuration and an externally threaded shank 14 having right-hand male fastener threads 16 defined thereon. A socket 18 of uniform, hexagonal cross-sectional configuration throughout is defined in the fastening screw head 12 remote from the shank 14 and in longitudinal alignment therewith.

Figure 2:
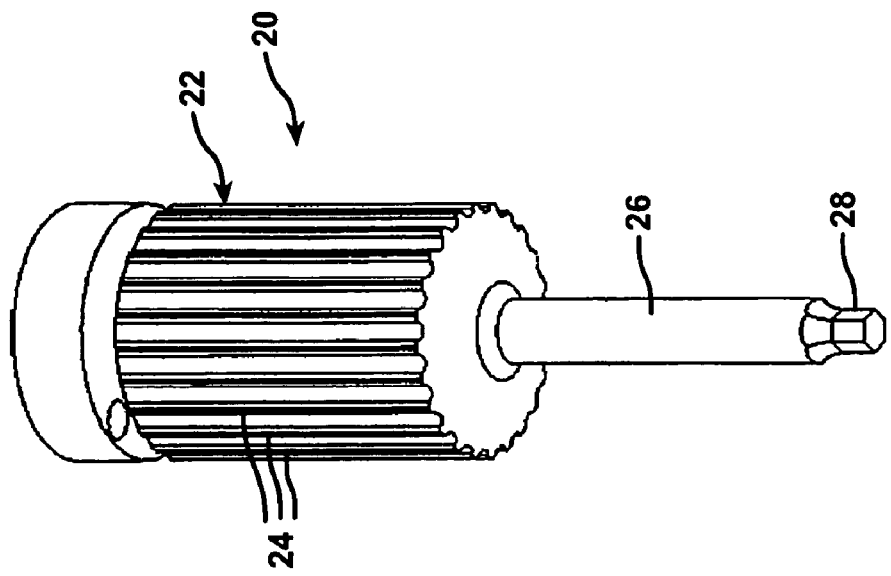
FIG. 2 is a perspective view of a conventional tool used to install and remove the dental implant screw of FIG. 1.

FIG. 2 illustrates a conventional osseodontic dental implant fastening screw installation and removal tool 20. The tool 20 includes a generally cylindrical, enlarged grip portion 22 having a multiplicity of longitudinally extending ribs 24 formed on its outer surface to provide improved traction for gripping the tool 20 and rotating it. An elongated, cylindrical rod 26 extends coaxially from the underside of the grip 22 and terminates in a distal tip 28 that has a hexagonal, uniform cross section of a size designed to fit snugly with in the socket 18 of the dental implant fastening screw 10, shown in FIG. 1. It is to be understood that the tool 20 is considerably larger in size than the dental implant fastening screw 10.

It is evident that a user may install and remove the fastening screw 10 by engaging the distal tip 28 in the socket 18 and rotating the grip 22 in a clockwise direction, as view from above, to install the fastening screw 10 to anchor an abutment to a dental implant member in an osseodontic dental implant system.

The tool 20 may also be utilized to remove the dental implant fastening screw 10 by engaging the distal tip 28 in the socket 18 and rotating the grip 22 in a counterclockwise direction. However once the threads 16 of the conventional fastening screw 10 have been completely disengaged from the implant threads and from the abutment threads, longitudinal withdrawal of the fastening screw 10 from the confines of the abutment passageway is difficult since longitudinal withdrawal of the tool 20 will pull the distal tip 28 out of the socket 18. There is thus a tendency for the fastening screw 10 to remain loose within the confines of the abutment passageway.

Figure 3:
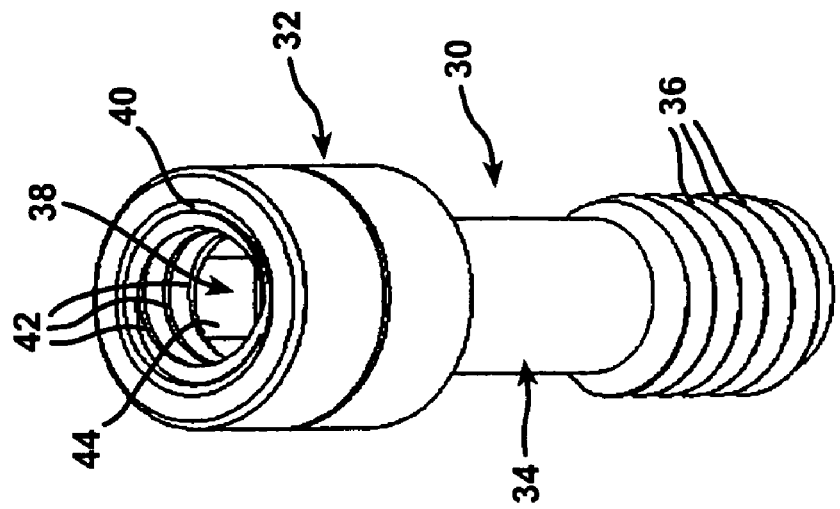
FIG. 3 is a perspective view of an improved dental implant fastening screw according to the present invention.

The present invention solves this dilemma of complete removal of the dental implant fastening screw by providing an improved dental implant fastening screw of unique construction. FIG. 3 illustrates one embodiment of a dental fastening screw 30 constructed according to the present invention. The dental implant fastening screw 30 differs in construction from the conventional dental implant fastening screw 10 in several respects. The dental implant fastening screw 30 has a cylindrical head 32 and a shank 34 of reduced diameter depending longitudinally therefrom. Right-hand male fastener threads 36 are defined on at least the portion of the shank 34 remote from the fastening screw head 32.

Figure 3A:
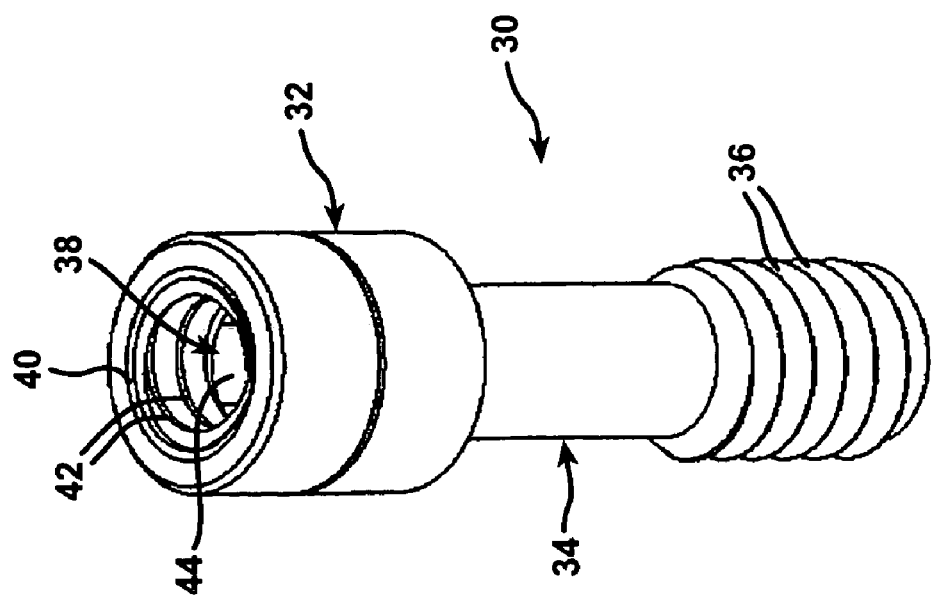
FIG. 3A is another perspective view of the dental implant screw of the invention shown in FIG. 3 as viewed from a somewhat different angle.

The fastening screw head 32 is located atop the shank 34 and is formed with an axial socket 38 therein. The socket 38 has a mouth 40 at which internal left-hand thread threads 42 are formed. Beneath the mouth 40 and further within its interior the socket 38 is configured with a noncylindrical cavity 44, which has a uniform hexagonal cross section. The hexagonal-shaped cavity 44 is located interiorly within the fastening screw head 32 beyond the mouth 40. The area of the hexagonal cavity 44 is smaller than the circular area encompassed by the threads 42 at the mouth 40 of the socket 38 so that the distal tip 28 of the tool 30 shown in FIG. 2 can still clear the threads 42 and can be inserted into the socket 38 to engage the walls of the hexagonal cavity 44. FIG. 3A is another view of the endosseous dental implant fastening screw 30 shown from a slightly different angle.

Figure 4:
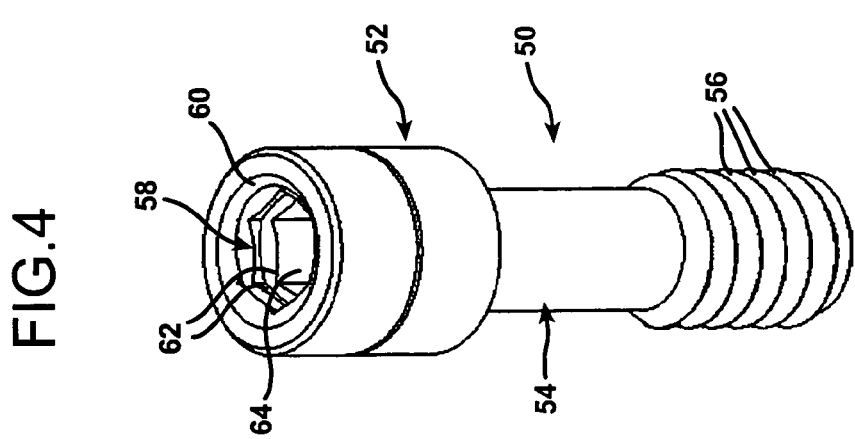
FIG. 4 is a perspective view of an alternative embodiment of a dental implant screw according to the invention.

FIG. 4 illustrates another embodiment of a dental implant fastening screw 50 according to the invention which is similar in some respects to the fastening screw 30. The dental implant fastening screw 50 has a head 52 with an outer, cylindrical configuration and a shank 54 depending therefrom. The fastening screw shank 54 has right-hand threads 56 defined on at least the portion of the shank 54 remote from the fastening screw head 52.

The fastening screw head 52 has an upwardly facing, noncylindrical socket 58 formed with a mouth 60 to the socket 58 having internal, left-hand threads 62 defined thereon. The deeper portion 64 of the socket 58 has smooth, flat walls and is shaped in a hexagonal configuration. The fastening screw 50 differs from the fastening screw 30 in that the socket 58 has a basically hexagonal configuration throughout its entire length, but has internal left-hand threads 62 defined in the mouth 60 of the socket 58, whereas the mouth 40 of the fastening screw 30 has an interior, circular area that circumscribes the area of the hexagonal cavity 44. However, operation and utilization of the different embodiments of the dental implant fastening screws 30 and 50 illustrated in the drawings is identical.

Figure 5:
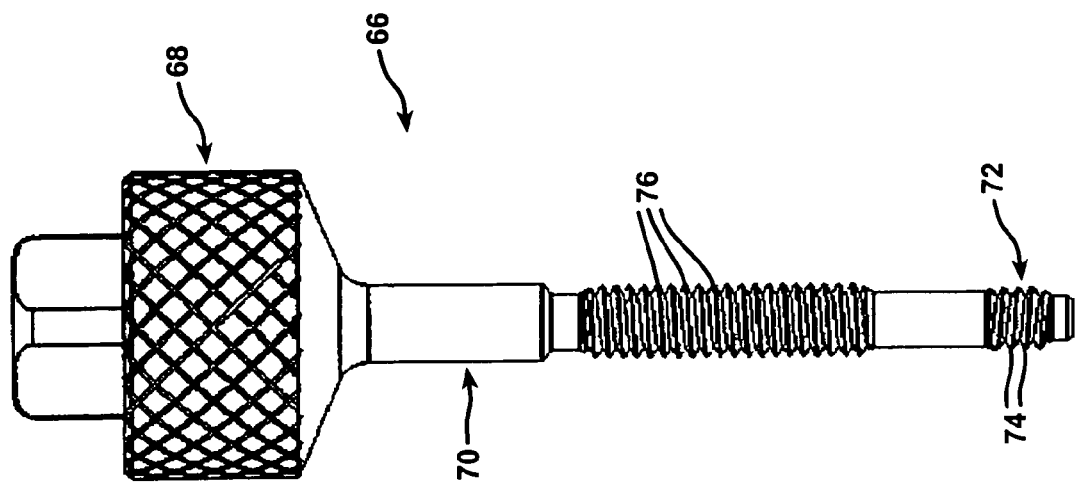
FIG. 5 is a side elevational view of an installation and removal tool according to the invention for use with the improved dental implant screws of FIGS. 3, 3A, and 4.

FIG. 5 illustrates an endosseous dental implant installation and extraction tool 66 which is designed to engage both the mouth 40 of the fastening screw 30 and the mouth 60 of the fastening screw 50. The installation and extraction tool 66 is comprised of a cylindrical-shaped grip 68 having a knurled outer surface so as to provide good gripping traction. The installation and extraction tool 66 has a shank 70 depending from the grip 68. The shank 70 is formed as a screw extraction rod having a distal tip 72 upon which external male left-hand threads 74 are formed. Between the distal tip 72 and the grip 68 external male right-hand threads 76 are formed on the shank 70. The right-hand threads 76 are engageable with the implant screw threads and with the abutment screw threads in an endosseous implant system.

Figure 6:
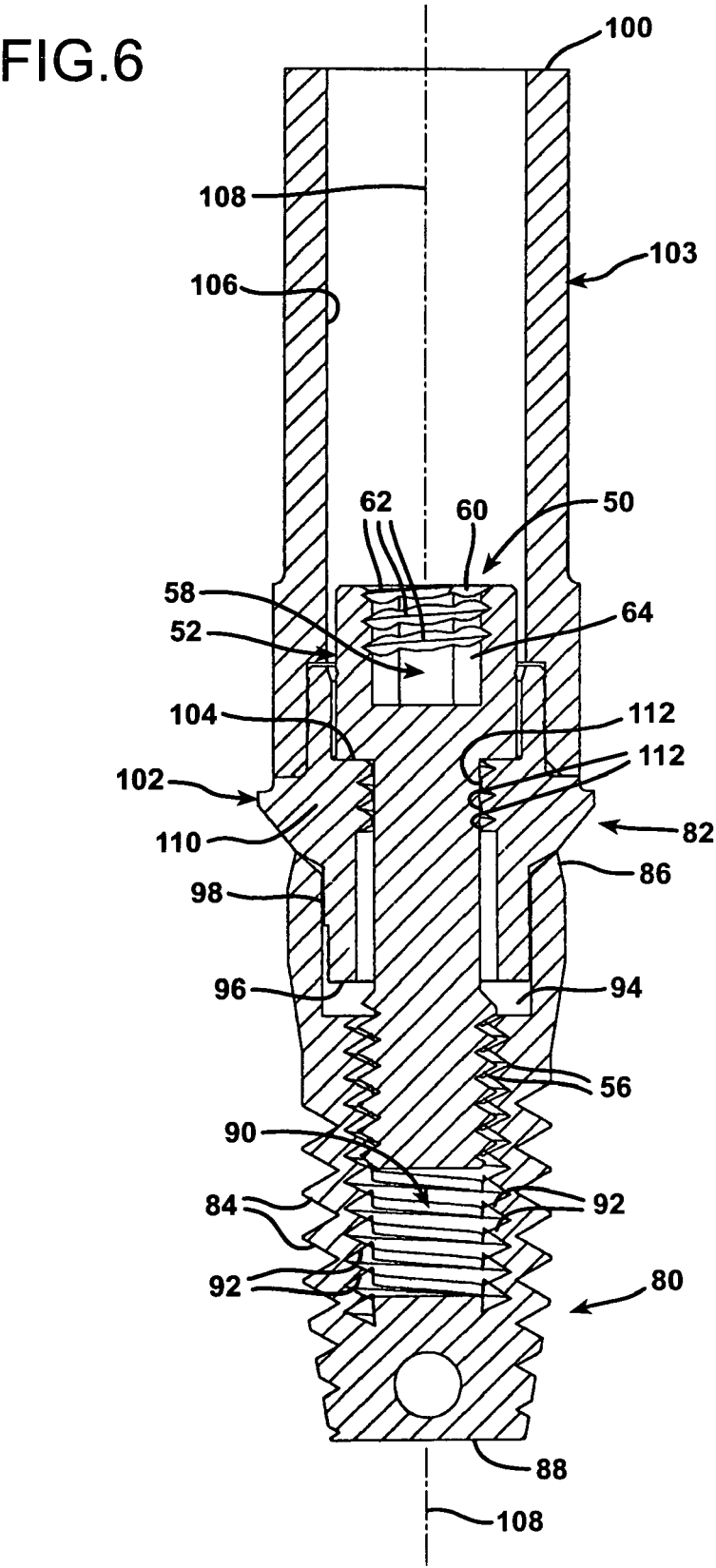
FIG. 6 is a side sectional elevational view illustrating the dental implant fastening screw of FIG. 4 installed in an osseodontic dental implant system.

FIG. 6 illustrates an endosseous dental implant system comprised of an endosseous dental implant member 80, a mating abutment member 82, and an endosseous dental implant fastening screw according to the invention, which, in FIG. 6, is the fastening screw 50 illustrated in FIG. 4.

The endosseous dental implant member 80 is typically fabricated as a titanium structure having external threads 84 designed to be screwed into the jaw bone of a patient and penetrate into the bone to anchor the implant member 80 relative to the patient's jaw. The implant member 80 has a gingival end 86 that resides at approximately the patient's gum line when the endosseous dental implant member 80 is implanted in a patient's jaw, and an opposite end 88 embedded in the patient's jaw. When the implant member 80 is installed in the jaw of a patient, the osseous end 88 penetrates well into the jaw bone structure of the patient.

Internally within the endosseous dental implant member 80 a longitudinal bore 90 is defined from the gingival end 86 toward the osseous end 88. Internal right-hand female implant screw threads 92 are defined spirally into the walls of the bore 90.

At the gingival end 86 of the dental implant member 80 a longitudinal socket 94 is defined. The socket 94 has a noncircular cross section, typically hexagonal. The socket 94 of the endosseous dental implant member 80 is formed as a cavity or well having a uniform, hexagonal cross section throughout its length. The upper end of the socket 94 is open at the gingival end 86 of the dental implant member 80.

The mating abutment member 82 has a gingival end 96 at which a post 98 is formed that fits snugly into the socket 94 of the endosseous dental implant member 80. The post 98 has a substantially hexagonal-shaped outer circumference that matches the shape of the socket 94 so as to prevent the abutment member 82 from twisting relative to the implant member 80. Preferably, the abutment member 82 is configured as described in my pending U.S. application Ser. No. 10/390,864 filed Mar. 18, 2003, which is hereby incorporated by reference in its entirety.

The abutment member 82 has an opposite coping end 100 that is directed outwardly away from the gingival end 96. An artificial tooth (not shown) is secured about the coping end 100 of the abutment 82.

The abutment 82 is shown as a two-part structure formed with a gold collar section 102 at its gingival end 96 and with a relatively long, plastic tubular casing or chimney structure 103 at its coping end 100. The sections 102 and 103 are permanently glued together. A longitudinal passageway 106 is defined throughout the length of the abutment member 82. The diameter of the passageway 106 is larger at the coping end 100 than at the gingival end 96 of the abutment member 82. At the transition between the enlarged diameter portion leading to the coping end 100 of the passageway 106 and the small diameter portion at the gingival end 96 thereof an upwardly facing, annular screw head bearing ledge 104 is created residing in a plane perpendicular to the longitudinal alignment of the dental implant member 80 and abutment member 82 along the common axis of alignment 108 thereof.

Proximate its gingival end 96 the collar section 102 of the abutment member 82 is provided with a necked-down region 110 adjacent the screw head bearing ledge 104. A plurality of right-hand female abutment screw threads 112 are formed within the passageway 106 at the necked-down region 110 of the abutment member 82. The abutment screw threads 112 have the same thread pitch and diameter as the implant screw threads 92 of the dental implant member 80. Also, the implant passageway 106 is longitudinally aligned with the bore 90 in the implant member 80 along the common, longitudinal axis of alignment 108.

A fastening screw according to the invention, such as the fastening screw 30 illustrated in FIG. 3 or the fastening screw 50 illustrated in FIG. 4, is employed to firmly attach the abutment member 82 to the implant member 80. The embodiment of the endosseous dental implant system illustrated in drawing FIGS. 6–10 is shown utilizing the dental implant fastening screw 50, illustrated in FIG. 4. As shown in FIG. 6, when the fastening screw 50 is installed in the endosseous dental implant system illustrated, the annular undersurface of the fastening screw head 52 is tightened to bear downwardly on the bearing ledge 104. To install the fastening screw 50 in this manner, the installation and removal tool 66 illustrated in FIG. 5 is first utilized.

While grasping the grip 68 of the tool 66 the user rotates the installation and removal tool 66 in a counterclockwise direction, as viewed from above, while pressing the distal end 72 of the tool 66 into the mouth 60 of the socket 64 of the fastening screw 50. This counterclockwise rotation causes the male left-hand threads 74 on the distal tip 72 of the tool 66 to engage the corresponding, mating female left-hand threads 62 in the head 52 of the fastening screw 50. The elongated shank of the tool 66 can then be inserted longitudinally into the abutment member 82 from the coping end thereof with the fastening screw 50 securely but releaseably attached to the distal tip 72 by virtue of the interengagement of the left-hand threads thereof.

As the right-hand threads 56 of the fastening screw 50 reach the threads 112 in the abutment member 82, continued clockwise rotation of the tool 66 and the fastening screw 50 advances the shank 54 of the fastening screw 50 past the abutment screw threads 112 and onward toward engagement with the right-hand screw threads 92 of the implant member 80. Continued clockwise rotation of both the tool 66 and the fastening screw 50 advances the externally threaded distal portion of the fastening screw shank 54 into engagement with the implant threads 92 defined in the bore 90 of the dental implant member 80.

The fastening screw 50 can be lightly tightened in this manner. However, continued clockwise rotation of the tool 66 relative to the abutment member 82 causes the left-hand threads 74 to unscrew and back out of engagement with the left-hand threads 62 of the fastening screw 50 once sufficient resistance occurs due to tightening of the right-hand male fastening screw threads 56 into firm engagement with the right-hand female screw threads 92 in the dental implant member 80. Continued clockwise rotation results in disengagement of the distal tip of the tool 66 with the threads 62 of the fastening screw 50.

At this point the conventional tool 20 is utilized to completely tighten the screw 50 relative to both the implant member 80 and the abutment member 82. After the tool 66 has been removed from engagement with head 52 of the fastening screw 50, the shank 26 of the tool 20 is inserted into the passageway 106 of the abutment member 82 at the coping end 100 thereof. The hexagonal tip 28 of the tool 20 engages the lower, unthreaded hexagonal portion 64 of the socket 58 so that the screw 50 can be advanced into very tight engagement with the implant member 80 by continued clockwise rotation of the tool 20 and the fastening screw 50 relative to the stationary implant member 80. Once the fastening screw 50 has been tightened, the tool 20 is longitudinally withdrawn.

When it is necessary to withdraw the fastening screw 50 from engagement with the implant member 80, the fastener installation and withdrawal tool 66 is utilized. The shank 70 of the tool 66 is inserted into the passageway 106 from the coping end 100 of the abutment member 82. Once the distal tip 72 of the tool 66 reaches the mouth 60 of the socket 58, the tool 66 is rotated in a counterclockwise direction, as viewed from above. This advances the tip 72 into the socket 58, since the left-hand threads 74 on the distal tip 72 of the tool 66 engage the left-hand threads 62 of the fastening screw 50. This initial counterclockwise rotation of the tool 66 relative to the fastening screw 50 creates a firm but temporary coupling between the distal end 72 of the tool 66 and the head 52 of the fastening screw 50.

Continued counterclockwise rotation of the tool 66 ultimately causes the fastening screw 50 to rotate in a counterclockwise direction as well, once the left-hand threads 74 and 62 of the tool 66 and fastener 50 have been engaged as far as possible. This continued counterclockwise rotation thereafter rotates the fastening screw 50 relative to the implant screw threads 92, thereby causing the fastening screw 50 to become unscrewed and back out of complete engagement with the implant threads 92.

Figure 7:
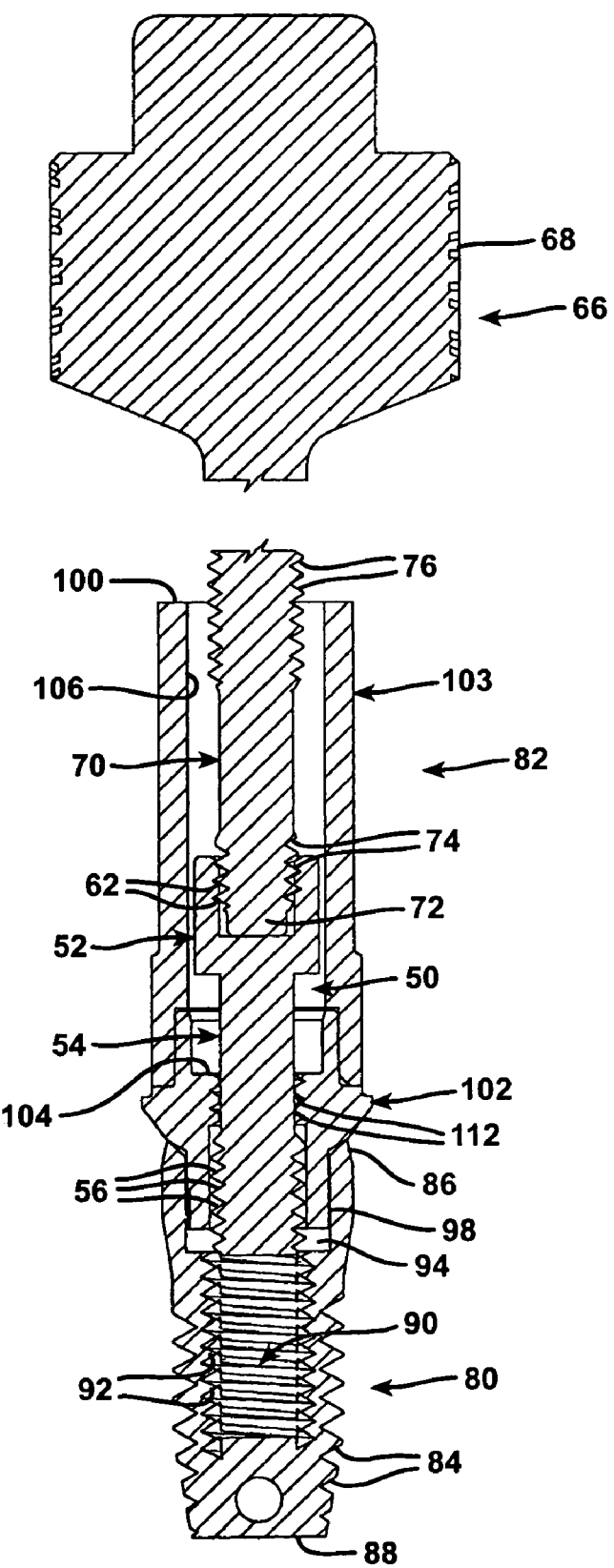
FIG. 7 is a side sectional elevational view illustrating the use of the tool of FIG. 5 in removing the dental implant fastening screw from the system shown in FIG. 6.

With continued counterclockwise rotation, the male, right-hand threads 56 of the fastening screw 50 are backed out of any engagement with the threads 92 of the implant member 80. This condition is illustrated in FIG. 7.

Continued counterclockwise rotation of the tool 66 causes the screw 52 to be retracted even further from engagement with the implant member 80 until the right-hand male threads 56 of the fastening screw 50 are disengaged completely from the mating, right-hand female screw threads 92 of the implant member 80. This condition is illustrated in FIG. 8.

Figure 8:
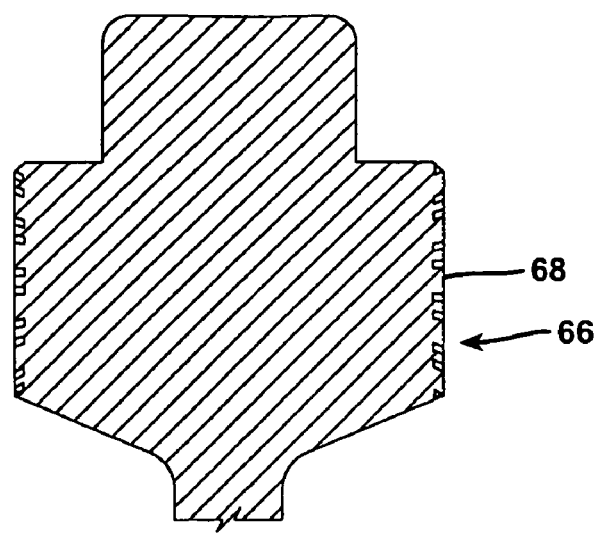
FIG. 8 is a side sectional elevational view that illustrates a further step in the removal of the dental implant fastening screw.
Figure 8:
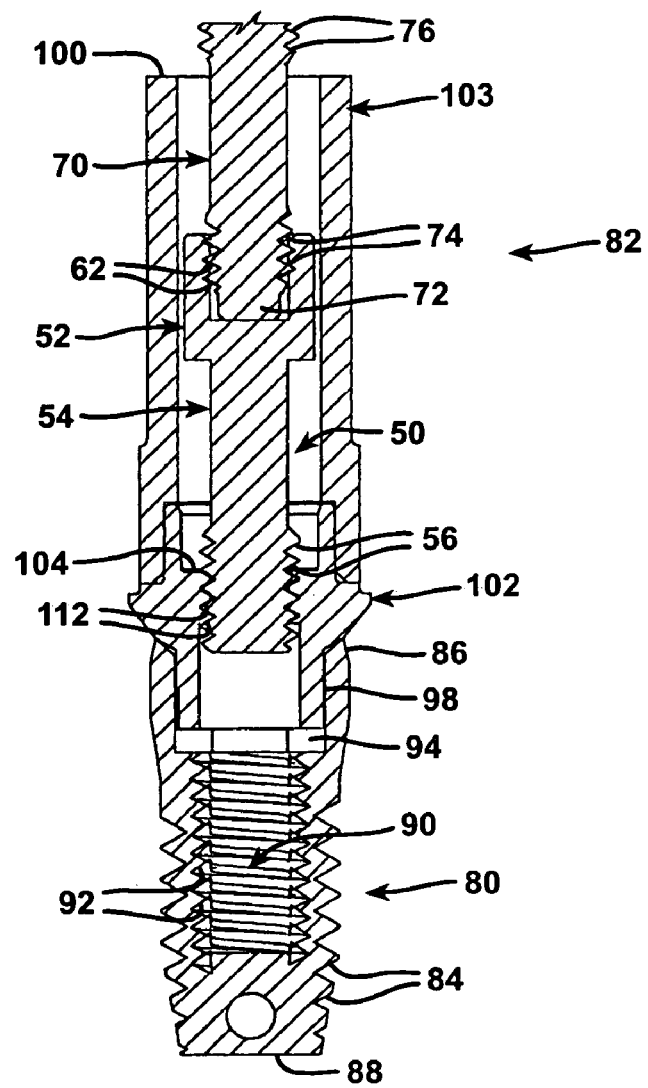
Figure 9:
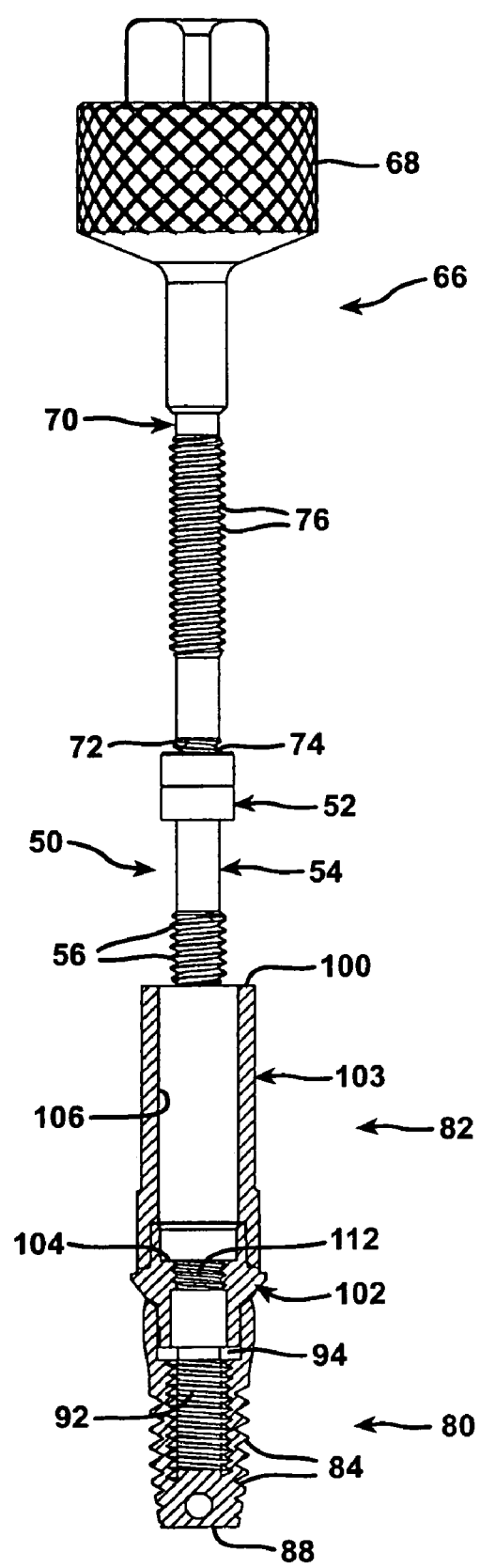
FIG. 9 is a side elevational view, partially in section, illustrating the fastening screw of the invention completely removed from the dental implant system.

Further continued counterclockwise rotation of the tool 66 backs the fastening screw 50 out of engagement with the threads 112 of the abutment member 82, thereby retracting the fastening screw 50 from the position illustrated in FIG. 8 to the fully retracted position illustrated in FIG. 9.

Figure 10:
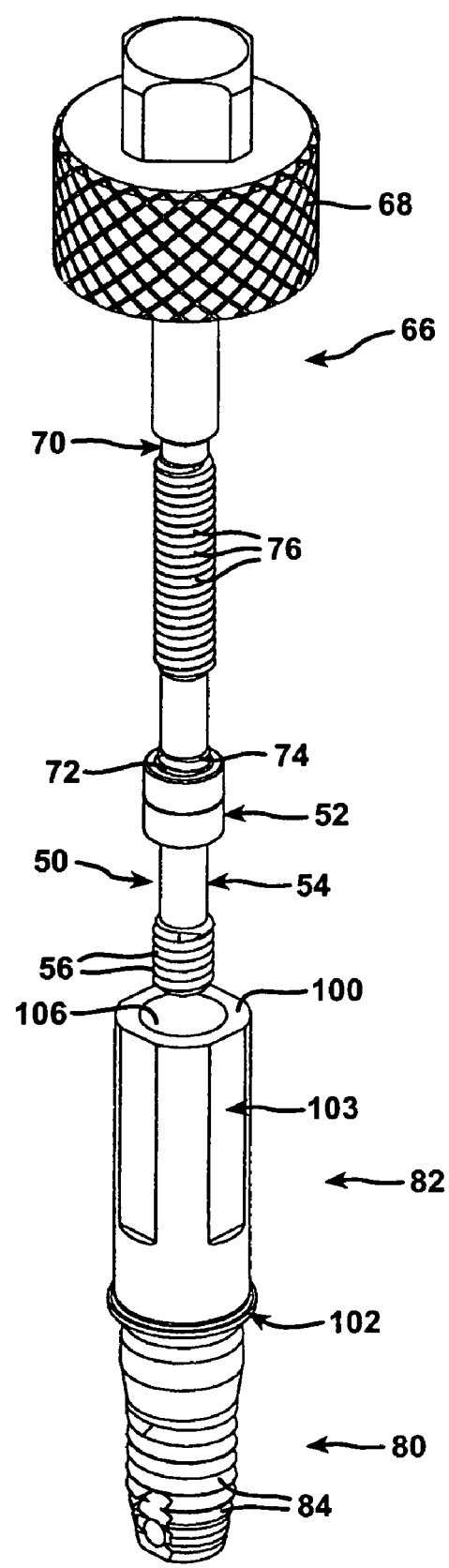
FIG. 10 is a perspective view illustrating the improved dental implant fastening screw of the invention completely removed from the dental implant and abutment.

Tt is important to note that once the right-hand threads 56 of the fastening screw 50 and the corresponding right-hand threads 112 of the abutment member 82 have been fully disengaged, the fastening screw 50 remains coupled to the distal tip 72 of the tool 66 by virtue of the continued interengagement of the left-hand threads 74 and 62 of the tool 66 and fastening screw 50, respectively. Unlike conventional system, the process of unthreading the fastening screw 50 from the abutment member 82 does not allow the screw 52 to remain in the passageway 106 even if the tool 66 is completely longitudinally withdrawn, as illustrated in FIG. 9. As is evident in that drawing figure, by virtue of the counterclockwise rotation of the tool 66, the fastening screw 50 remains fully engaged on the distal tip 72 of the tool 66. The fastening screw 50 can thereupon be completely withdrawn from the passageway 106, as illustrated in FIGS. 9 and 10. The tool 66 can thereupon be disconnected from the fastening screw 50 by rotating the tool 66 in a clockwise direction relative to the fastening screw 50, while holding the fastening screw 50 immobile. This causes the distal tip 72 to unscrew and back out of engagement with the left-hand threads 62 in the mouth 60 of the socket 58.

It is to be understood that numerous other variations and modifications of the invention are possible. For example, the orientation of the threads could be reversed. That is, the implant screw threads 92 and abutment screw threads 112, as well as the screw threads 56 on the shank 54 of the fastening screw 50 could be left-hand threads. In that case, the screw threads 62 in the mouth 60 of the socket 58 and the threads 74 on the distal tip 72 of the tool 66 would have to be right-hand threads in order for the system to operate in an equivalent manner. Also, the screw could have a protruding noncylindrical post instead of a head with a socket. In that case the threads on the post would be male threads and the threads at the tip of the tool of the invention would be female threads. Such modifications would indeed be the equivalent of the preferred embodiments of the invention illustrated and described. However, the embodiments of the invention depicted and described are highly preferred because they adopt the existing convention of employing right-hand threads on the shank of a dental implant fastening screw that engages corresponding right-hand implant screw threads and right-hand abutment screw threads. Also, the screw of the invention is not limited to an abutment screw, but also includes coping screws, fastening screws, and any other type of screw utilized in the field of osseodontic dental implants.

Other modifications of the invention are also possible. Accordingly, the scope of the invention should not be construed as limited to the specific embodiments illustrated and described, but rather is defined in the claims appended hereto.

I claim:

1. An endosseous dental implant fastening screw comprising a shank with right-hand male threads defined thereon and a fastening screw head located atop said shank and formed with an axial socket therein and said socket has a mouth at which internal female left-hand threads are formed, and a noncylindrical cavity located internally within said fastening screw head beyond said mouth.

2. An endosseous dental implant fastening screw according to claim 1 wherein said noncylindrical cavity has a hexagonal cross section.

3. An endosseous dental implant system comprising:
an endosseous dental implant member having a longitudinal bore with internal right-hand female implant screw threads defined therein,
a mating abutment member having a longitudinal passageway defined throughout its length and said implant passageway is longitudinally aligned with said bore in said dental implant member and said passageway has an upper end of enlarged diameter thereby defining an upwardly facing, annular screw head bearing ledge, and
a fastening screw having a head with a shank depending therefrom, wherein said fastening screw shank has right-hand threads thereon engageable with said implant screw threads and said fastening screw head has an upwardly facing noncylindrical socket formed with a mouth to said socket having internal left-hand threads defined thereon.

4. An endosseous dental implant system according to claim 3 further comprising an installation and extraction tool for engaging said mouth of said socket comprising a grip with a shank extending therefrom formed as a screw extraction rod having a distal tip with external, male, left-hand threads thereon engageable with said left-hand threads at said socket mouth of said fastening screw are formed on said distal tip of said shank of said installation and extraction tool.

5. An endosseous dental implant system according to claim 4 wherein said noncylindrical socket in said screw head has a hexagonal cross section.

6. In combination,
an endosseous dental implant member having a longitudinal bore with internal right-hand female implant threads defined thereon,
a mating abutment member having a longitudinal passageway defined throughout its length wherein said implant bore and said abutment passageway are longitudinally aligned with each other, and said passageway has a mouth of enlarged cross section remote from said implant, and an annular fastening screw head bearing ledge is defined in said passageway,
an implant fastening screw having a head and a shank depending therefrom, and said shank has external, right-hand, male fastener threads defined thereon and said head has a longitudinally extending socket defined therein including a mouth portion with female, left-hand extraction threads defined therein and a portion of noncircular cross-sectional area beneath said mouth portion, and
an endosseous dental implant fastening screw installation and removal tool for engaging and disengaging said implant fastening screw with said implant member and said abutment member, wherein said tool has a grip and an elongated rod with a distal tip remote from said grip and including left-hand threads on said distal tip and right-hand threads on said elongated rod between said grip and said distal tip.

7. An endosseous dental implant apparatus comprising:
an endosseous dental implant member having a longitudinal bore with internal right-hand female implant threads defined thereon,
a mating abutment member having a longitudinal passageway defined throughout its length wherein said implant bore and said abutment passageway are longitudinally aligned with each other, and said passageway has a mouth of enlarged cross section remote from said implant, and an annular fastening screw head bearing ledge is defined in said passageway, and an implant fastening screw having a head and a shank depending therefrom, and said shank has external, right-hand, male fastener threads defined thereon and said head has a longitudinally extending socket defined therein including a mouth portion with female, left-hand extraction threads defined therein and a portion of noncircular cross-sectional area beneath said mouth.

8. An endosseous dental implant apparatus according to claim 7 wherein said noncircular portion of said socket has a hexagonal shape.

9. An endosseous dental implant apparatus according to claim 8 further comprising a fastening screw installation and removal tool having a grip and an elongated rod with a distal tip remote from said grip and including left-hand threads on said distal tip for engaging said female threads in said mouth portion of said socket.

10. An endosseous dental implant apparatus according to claim 7 wherein said passageway through said abutment member has a necked-down region at which internal abutment threads are formed.

11. An endosseous dental implant apparatus according to claim 7 wherein said mouth of said socket has a hexagonal cross section with said female left-hand threads formed therein.

12. An endosseous dental implant apparatus according to claim 7 wherein said mouth of said socket has a circular shape and said portion of noncircular cross section has a cross-sectional area less than the cross-sectional area of said mouth.

13. An endosseous dental implant fastening screw comprising a shank with right hand male threads defined thereon and a fastening screw head located a top said shank and formed with an axially projecting post of non cylindrical cross section having a tip upon which male left-hand threads are formed.

14. An endosseous dental implant apparatus according to claim 13 further comprising a fastening screw installation and removal tool having a grip and an elongated rod with a distal tip remote from said grip and including a socket with female left-hand threads on said distal tip for engaging said male threads on said post of said screw head.

* * * * *